United States Patent [19]
Shorr et al.

[11] Patent Number: 5,650,388
[45] Date of Patent: *Jul. 22, 1997

[54] FRACTIONATED POLYALKYLENE OXIDE-CONJUGATED HEMOGLOBIN SOLUTIONS

[75] Inventors: Robert G. L. Shorr, Edison; Carl W. Gilbert, Basking Ridge, both of N.J.

[73] Assignee: Enzon, Inc., Piscataway, N.J.

[*] Notice: The term of this patent shall not extend beyond the expiration date of Pat. No. 5,312,808.

[21] Appl. No.: 497,031

[22] Filed: Jun. 30, 1995

Related U.S. Application Data

[63] Continuation-in-part of Ser. No. 146,847, Nov. 3, 1993, Pat. No. 5,478,805, which is a continuation of Ser. No. 960,007, Oct. 13, 1992, Pat. No. 5,312,808, which is a continuation-in-part of Ser. No. 616,129, Nov. 20, 1990, Pat. No. 5,234,903, which is a continuation-in-part of Ser. No. 440,553, Nov. 22, 1989, abandoned.

[51] Int. Cl.$^6$ ............................ A61K 38/42; C07K 14/05
[52] U.S. Cl. ................................................ 514/6; 530/385
[58] Field of Search .................................. 514/6; 530/385

[56] References Cited

U.S. PATENT DOCUMENTS

| | | | |
|---|---|---|---|
| 4,001,401 | 1/1977 | Bonsen et al. | 424/177 |
| 4,764,279 | 8/1988 | Tayot et al. | 436/175 |
| 5,234,903 | 8/1993 | Nho et al. | 514/6 |
| 5,312,808 | 5/1994 | Shorr et al. | 514/6 |
| 5,478,805 | 12/1995 | Shorr et al. | 514/8 |

FOREIGN PATENT DOCUMENTS

| | | |
|---|---|---|
| 0067029A3 | 12/1982 | European Pat. Off. |
| 0132178A1 | 1/1985 | European Pat. Off. |
| 0206488A1 | 12/1986 | European Pat. Off. |
| 2055868 | 3/1981 | United Kingdom |
| 2221911 | 2/1990 | United Kingdom |
| WO91/07190 | 5/1991 | WIPO |
| WO91/09615 | 7/1991 | WIPO |
| WO92/03153 | 3/1992 | WIPO |
| WO92/08478 | 5/1992 | WIPO |

OTHER PUBLICATIONS

Dellacherie, E. et al., "Hemoglobin–based artificial blood: new polymeric derivatives of hemoglobin with low oxygen affinity", The Int'l. Journal of Artificial Organs/vol. 14/No. 1, 1991/pp. 28–32.
Larude, P. et al., "Hemoglobin solutions coupled with ployethylene glycol 1900", The Int'l. Journal of Artificial Organs./vol. 11/No. 5, 1988/pp. 383–402.
Menu, P., et al., "Possible Importance of Chromatographic Purification Position in a Blood Substitute Elaboration Process", Bio–Mat., Art.Cells & Immob. Biotech., 20(2–4), 443–445 (1992).
Iwasaki, Keiji, et al. "Preparation and Evaluation of Hemoglobin–Polyethylene Glycol Conjugate as an Oxygen–Carrying Resuscitation Fluid", Artificial Organs, 10(5): 411–416 (1986).
Takahashi, et al. Artificial Organs 15(6) 462–473 (1991).
Labrude, P. et al. Int'l. J. Artificial Organs vol. 11 No. 5(1988) 393–402.
Leonard, et al. Tetrahedron vol. 40, No. 9 pp. 1581–1584 (1984).
Dellacherie, E. et al. The Int'l. J. Artificial Organs vol. 14, No. 1 pp. 28–32 (1991).
Dellacherie, E. et al. Makromol. Chem. Suppl. 9 pp.43–46 (1985).
Leonard, M. et al. Biochemica et Biophysica Acta 791 pp. 219–225 (1984).
Matsushita, M. et al. vol. XXXIV Trans. Am. Soc. Artif. Intern Organs (1988) pp. 280–283.
Agishi, T. et al. Biomat., Art. Cells, Art. Org. 16(1–3) 261–270 (1988) 261–270.
Nishi, K., et al. Biomat., Art. Cells, Art Org., 16(1–3) (1988) 653–655.
Iwasaki, K., et al. Artificial Organs 10(5) pp. 411–416 (1986).
Ajisaka, K., et al. Biochemical and Biophysical Communications vol. 97, No. 3 Dec. 16, 1980 pp. 1076–1081.
Conover, C., et al "PEG–Hemoglobin effects on blood pressure and heart rate in the dog" 1993 IBC Blood Substitutes & Related Products.
Conover, C., et al "Vascular persistence of polyethylene glycol (PEG) modified hemoglobin in rats and dogs 1993 IBC Blood Substitutes & Related Products".
Nho, K., et al. "Increased Oxygen Tension in Solid Tumors Following PEG–Hemoglobin Infusion" 1993 IBC Blood Substitutes & Related Products.
PEG–Modified Hemoglobin is Exchange Transfused in Non–Shock Rat Model Abstract 3372 Fuel Metabolism I FASEBJ 6(4) PA1518 (1992).
Nho, K., et al. Poly(Ethylene Glycol) Chemistry: Biotechnical and Biomedical Applications, pp. 171–182; Harris, J. Ed. (1992).
Kide, Y., et al., "Vascular Responsiveness to Various Vasoactive Substances After Exchange Transfusion . . . " Artificial Organs 15(1) 5–14 (1991).
Matsuzawa, Y., et al. "Metabolic Rate of Pyridoxylated Hemoglobin Polyoxyethylene Conjugate in Rats and Dogs" Abstract PP1493, Pharm. Res.6(9) 1989.
Yabuki, A., et al. "Characterization of a Pyridoxylated Hemoglobin–Polyoxyethylene Conjugate as a Physiologic Oxygen Carrier" Transfusion 1990 vol. 30 No. 6 pp. 516–520.

(List continued on next page.)

*Primary Examiner*—Cecilia J. Tsang
*Assistant Examiner*—Anish Gupta
*Attorney, Agent, or Firm*—Michael N. Mercanti

[57] ABSTRACT

Polyalkylene oxide-conjugated hemoglobin solutions having a molecular weight greater than about 85,000 daltons and a degree of substitution of which substantially avoids clinically significant nephrotoxicity associated with hemoglobinuria in mammals. A method of simultaneously fractionating and purifying polyalkylene oxide-conjugated hemoglobins is al so disclosed.

51 Claims, No Drawings

OTHER PUBLICATIONS

Cerny, L., et al. "A Potential Blood Substitute From A Tetronic Polyol and a Modified Hemoglobin" Biomat., Art. Cells & Immob. Biotech., 20(1) 71–93 (1992).

Iwashita, Y., et al. "Renal Toxicity of Hemoglobin Derivatives as Blood Substitute" p. 97, et seq. citation and date unavailable.

Iwashita, Yugi, et al., "Renal Toxicity of Hemoglobin Derivatives As Blood Substitute", Miscellaneousi (5 Mar. 1981) Abstract A11.

Iwashita, Y., et al., "A New Resuscitation Fluid Stabilized Hemoglobin" Preparation and Characteristics, Biomat. Art. Cells. Art Org. 16(1–3) 271–280 (1988).

Agishi, T., et al. "Modified Hemoglobin Solution As Possible Perfusate Relevant To Organ Transplantation", Biomat. Art. Cells & Immob. Biotech. 20(2–4), 539–544 (1992).

Iwashita, Yuji, et al., "Relationship Between Chemical Properties and Biological Properties of Pyridoxalated Hemoglobin–Polyoxyethylene", Biomat., Art. Cells & Immob. Biotech., 20(2–4), 299–307 (1992).

Nho, Kwang, et al., "PEG–Bovine Hemoglobin: Safety In a Canine Dehydrated Hypovolemic–Hemorrhagic Shock Model", Biomat., Art. Cells & Immob. Biotech, 29(2–4), 511–524 (1992).

Matsumaura, Hioroaki, et al., "Pyridoxalated Hemoglobin Polyoxyethylene Conjugage (PHP) On the Encothelium-Dpendent Relaxation In Rat Mesenteric Arteriorles. Biomat., Art. Cells & Immob. Biotech.", 20(2–4), 679–681 (1992).

Matsumura, S., et al. "Large Scale Production And Characterization Of Lyophilized Pyridoxataed Hemoglobin–Polyoxyethylene (PHP), Biomat., Art. Cells & Immob. Biotech.", 20(2–4), 435–438 (1992).

Gilbert, C., et al. "Hemoglobinuria In Rats: A Sensitive Test Of Renal Filtering And Absorption Of PEG–Hemoglobin, A Red Blood Cell Substitute, Art. Cells, Blood Subs., and Immob. Biotech." 22(3), 535–541 (1994).

Bradley, R., "Production Of PEG–Modified Bovine Hemoglobin: Econimics And Feasbility", Art. Cells, Blood Subs., And Immob. Biotech., 22(3), 657–667 (1994).

Nho, K., et al., "PEG–Hemoglobin–An Efficient Oxygen–Delivery System In The Rat Exchange Transfusion And Hemovolmeic Shock Models, Art, Cells, Blood Subs., And Immob. Biotech.", 22(3), 795–803 (1994).

Linberg, R., et al., "Normal Oxygen–Tension Restored In The Ishemic Rat Liver Model By PEG–Hemoglobin, Art. Cells, Blood Subs., And Immob. Biotech.", 22(3), 805–812 (1994).

Malchesky, P.S., et al., Conjugated human hemoglobin as a physiological oxygen carrier —pyridoxalated hemoglobin polyoxyethylene conjugate (PHP), The International Journal of Artificial Organs, vol. 13, No. 7, 1990, pp. 442–450.

Lee, W.Y., et al. "Suppression of Reaginic Antibodies", Immunologial Rev. (1978), v.l. 41.

Takahashi, T., et al., "Renal Effects of Multiple Infusion of Pyridoxalated–Hemoglobin–Polyoxyethylene Conjugate (PHP) Solution in Dogs, Artificial Organs", 17(3): 153–169 (1993).

FRACTIONATED POLYALKYLENE OXIDE-CONJUGATED HEMOGLOBIN SOLUTIONS

CROSS-REFERENCES TO RELATED APPLICATIONS

This application is a continuation-in-part of U.S. patent application Ser. No. 08/146,847, filed Nov. 3, 1993, now U.S. Pat. No. 5,478,805, which is a continuation of U.S. patent application Ser. No. 07/960,007, filed Oct. 13, 1992, now U.S. Pat. No. 5,312,808, which is a continuation-in-part of U.S. patent application Ser. No. 07/616,129, filed Nov. 20, 1990, now U.S. Pat. No. 5,234,903, which, in turn, is a continuation-in-part of U.S. patent application Ser. No. 07/440,553, filed on Nov. 22, 1989, now abandoned. The disclosures of each of these application is incorporated herein by reference.

BACKGROUND OF THE INVENTION

The present invention relates to polyalkylene oxide-conjugated hemoglobins which substantially avoid causing hemoglobinuria in mammals. The present invention also relates to methods for separating the conjugated hemoglobins by degree of polyalkylene oxide substitution while removing endotoxins and phospholipids.

Advances have occurred in recent years in the development of hemoglobin-based blood substitutes. Such transfusional fluids serve as alternatives to whole blood or blood fractions for use as oxygen carriers and plasma expanders. The use of whole blood and blood fractions has grown increasingly disfavored because of the risk of immune or non-immune reactions and infections, such as acquired immunodeficiency syndrome.

The conjugation of polyethylene glycol (PEG) to hemoglobin reduces its antigenicity and extends its residence time in circulation. However, gross hemoglobinuria was reported by Iwashita and Ajisaka, *Organ-Directed Toxic.: Chem. Indicies Mech., Proc. Symp.*, (Brown et al., Eds. Pergamon, Oxford, England 1981), 97–101 in exchange-transfused rats receiving PEG-conjugates of hemoglobin monomeric subunits below 40,000 daltons. The PEG-conjugation reaction had resulted in dissociation of the hemoglobin tetramer into monomer subunits.

When conjugates having molecular weights over 50,000 daltons were infused, hemoglobinuria was not observed. However, Ajisaka and Iwashita, *Biochem. Biophys. Res. Comm.*, 97(3), 1076–81 (1980) disclosed that these PEG-conjugates of monomeric hemoglobin subunits had $P_{50}$'s between 9.5 and 12 mm Hg. Many skilled in the art believe that such a high oxygen affinity is inefficient for delivering oxygen to tissues.

Iwasaki and Iwashita, *Artif. Organs*, 10(5), 411–16 (1986) disclose the preparation of pyridoxalated PEG-hemoglobin conjugates. The conjugates have weight average molecular weights of 123,000±18,000 daltons and four to five PEG conjugates per hemoglobin molecule. However, this material still exhibited a 5% excretion rate into the urine over a 24 hour period when infused into rats.

U.S. Pat. No. 4,301,144 discloses various polyalkylene oxide hemoglobin conjugates with polyalkylene oxides having molecular weights between about 300 and about 20,000 daltons. The degree of substitution is between about 4 and about 120 polyalkylene oxide conjugates per hemoglobin molecule. The conjugate is disclosed as having a circulating half-life of two to four times longer than unmodified stroma-free hemoglobin.

U.S. Pat. No. 4,412,989 discloses various effector molecule modified hemoglobins conjugated to polyalkylene oxides. The polyalkylene oxides have molecular weights between about 300 and about 20,000 daltons and a degree of substitution between about 1 and about 20 conjugates per hemoglobin. A circulating half-life of four to seven times greater than stroma-free hemoglobin is reported.

U.S. Pat. No. 4,670,417 reports the unsuitability of the hemoglobin-polyalkylene oxide conjugates of U.S. Pat Nos. 4,301,144 and 4,412,989 because the hemoglobin also denatures during reaction with the polyalkylene oxide. The conjugation of various hemoglobins to polyalkylene oxides with carboxyl alkylene ether groups is offered as a solution. Four to six polyalkylene oxide conjugates per hemoglobin are formed, depending upon whether a dimeric or trimeric intermolecularly crosslinked conjugate is formed. The polyalkylene oxides disclosed range in molecular weight from 300 to 20,000 daltons, and the hemoglobin can be modified with effector molecules. The conjugation of polyalkylene oxides to hemoglobin via carboxyl alkylene ether linkages, however, is commercially impractical.

Without being bound by any particular theory, it is believed that the prior art overlooked the possibility that particular low-molecular weight polyalkylene oxide-hemoglobin conjugates were a cause of hemoglobinuria. The present invention addresses this need.

SUMMARY OF THE INVENTION

It has now been discovered that clinically significant hemoglobinuria associated with certain blood substitutes after administration is substantially eliminated by administering polyalkylene oxide-hemoglobin conjugates having a molecular weight greater than 85,000 daltons and a degree of polyalkylene oxide substitution which provides sufficient steric hindrance in the renal tubules. The molecular weight feature, in combination with the degree of substitution, provides a polyalkylene-oxide conjugated hemoglobin molecule that is sterically hindered from renal filtration by shape, mass and/or charge and thus does not readily cause hemoglobinuria and thus nephrotoxicity in mammals. Thus, the hemoglobin-containing solutions of the present invention comprise a polyalkylene oxide conjugated hemoglobin having a molecular weight and a degree of substitution which are sufficient to substantially avoid nephrotoxicity in mammals after administration of such solutions to mammals in need thereof. In these aspects of the invention, the hemoglobin conjugates have a molecular weight of at least about 85,000 daltons.

In one aspect of the invention, there are provided solutions containing polyalkylene oxide-conjugated hemoglobins having a molecular weight greater than about 85,000 daltons and a degree of substitution of at least five polyalkylene oxide conjugates per hemoglobin molecule.

In another aspect of the invention, there are provided solutions containing polyalkylene oxide-conjugated hemoglobins having a molecular weight greater than about 85,000 daltons and a degree of polyalkylene oxide substitution which is sufficient to avoid clinically significant nephrotoxicity associated with hemoglobinuria in mammals. In this aspect of the invention, the polyalkylene oxide strands selected for conjugation to the hemoglobin are of a sufficient molecular weight and number to meet the mass, charge and steric hindrance requirement to avoid hemoglobinuria in excess of 1% of the administered dose or 1 mg/ml of hemoglobin in the urine collected from 0 to 24 hours after administration.

The present invention also includes a method for fractionating solutions containing polyalkylene oxide-hemoglobin conjugates of mixed degrees of substitution. This method takes advantage of the fact that the isoelectric point of a conjugated hemoglobin molecule will vary by the degree of polyalkylene oxide substitution.

The present method also takes advantage of the fact that polyalkylene oxide-hemoglobin conjugates of varying degrees of substitution can be bound to a variety of anionic stationary phases. By elution under appropriate conditions of buffer ionic strength and pH, the conjugates can be resolved into fractions varying only by the degree of substitution.

It has also been unexpectedly discovered that the anionic stationary phases and conditions suitable for the fractionation of solutions of mixed polyalkylene oxide-hemoglobin conjugates will also result in the binding and thus the removal of physiologically unacceptable materials such as DNA, endotoxins or phospholipids from the solutions. Therefore, the present invention provides a method for simultaneous fractionation and purification of polyalkylene oxide-hemoglobin (PAO-Hb) conjugates.

The method includes:

contacting the PAO-Hb conjugates in solution with an anion exchange resin capable of selectively binding PAO-Hb conjugates having a molecular weight of less than about 85,000 daltons and an undesired degree of substitution, i.e., those which will cause nephrotoxicity due to excessive hemoglobinuria, such as those of less than five polyalkylene oxide strands of about molecular weight 5,000 or less per hemoglobin molecule and physiologically unacceptable materials, so that fractions of conjugated hemoglobin having molecular weights greater than about 85,000 daltons and the desired degrees of substitution, i.e., greater than five polyalkylene oxide conjugates of MW 5,000 or less per hemoglobin molecule are not bound by the resin and recovering the fractions of conjugated hemoglobins not bound by the resin.

Preferably, the anion exchange resin used in the carrying out of the simultaneous fractionation/purification process is coated with a quaternary amine.

The above-described method separates the polyalkylene oxide-hemoglobin conjugates of the present invention from lower molecular weight, less substituted fractions, and also serves as a final purification of the conjugates of any endotoxins or phospholipids.

As a result of the present invention, it is possible to provide hemoglobin solutions which substantially avoid the problems of clinically significant nephrotoxicity and hemoglobinuria, as well as other toxicities associated with prior art modalities. Moreover, the PAO-Hb conjugates can be purified and fractionated to precise molecular weight ranges and degree of substitution with a single anion exchange chromatography resin-elution buffer combination.

For purposes of the present invention, the term "clinically significant nephrotoxicity" shall be understood to mean a reduction in urine output of at least about 25-50% and ultimately renal failure.

Also for purposes of the present invention, the term "hemoglobinuria" shall be understood to mean the presence of at least 1% of the administered dose of the hemoglobin in the urine when the urine is collected over 0 to 24 hours after administration.

DETAILED DESCRIPTION OF THE PREFERRED EMBODIMENT

The polyalkylene oxide-hemoglobin (PAO-Hb) conjugates of the present invention overcome the hemoglobinuria problems associated with prior art compositions when administered to mammals. The conjugates are preferably administered in physiologically-acceptable solutions. In one aspect of the invention, the conjugates have molecular weights greater than about 85,000 daltons and degrees of substitution of five polyalkylene oxides or greater. In a separate aspect, the PAO-Hb conjugates have a molecular weight of greater than about 85,000 and a sufficient number of PAO strands conjugated to the hemoglobin so that the desired molecular weight of the conjugate is achieved.

In still further aspects of the invention, there are provided polyalkylene oxide-conjugated hemoglobin-containing solutions comprising polyalkylene oxide-conjugated hemoglobin having a molecular weight and a degree of substitution which are sufficient to substantially avoid nephrotoxicity in mammals after administration thereof.

Yet another aspect of the invention includes polyalkylene oxide-conjugated hemoglobin-containing solutions comprising polyalkylene oxide-conjugated hemoglobin having a molecular weight greater than about 85,000 daltons and a degree of substitution which is sufficient to substantially avoid nephrotoxicity in mammals after administration thereof.

The amount of the PAO-Hb conjugate in the solutions of the present invention may vary according to the needs of the artisan. It is contemplated, however, that in most situations, the hemoglobin solutions contain from about 1.0 to about 10.0 weight percent of the polyalkylene oxide-hemoglobin conjugates. More preferred solutions contain from about 3 to about 7.0 weight percent of the conjugates, with amounts of from about 4.0 to about 6.0 weight percent being most preferred.

The average degree of substitution, and consequently the average molecular weight, may be determined by trinitrobenzene sulfonic acid (TNBS) assay. This technique is well-known and essentially conventional. The molecular weight is determined by multiplying the average number of conjugates by the molecular weight of the polyalkylene oxide. This is then added to the molecular weight of the hemoglobin, approximately 64,000 daltons. The molecular weight may also be determined by multi-light channel laser light scattering techniques, which are also essentially conventional.

The molecular weight and degree of substitution should be chosen so that the viscosity of the solutions do not exceed physiological blood viscosity of the mammal administered the solution. For humans, this viscosity ranges from about 4.5 to about 5.0 cps. at 37° C.

Preferred solutions contain polyalkylene oxide-hemoglobin conjugates with molecular weights between about 90,000 and about 250,000 daltons, with molecular weights of from about 95,000 to about 120,000 daltons being most preferred. These solutions are also preferably substantially free of polyalkylene oxide-hemoglobin conjugates having molecular weights below the preferred ranges. Some preferred solutions are also limited to conjugates having an average degree of substitution of at least about 9 conjugates per hemoglobin molecule. More preferred solutions are limited to conjugates having an average degree of substitution of at least about 11 conjugates per hemoglobin molecule.

In one aspect of the invention, preferred solutions are substantially free of polyalkylene oxide-hemoglobin conjugates having degrees of substitution below the preferred ranges, that is, free of PAO-Hb conjugates which are associated with nephrotoxicity caused by hemoglobinuria. For purposes of the present invention, substantially free means that the solutions contain no more than about five weight percent of the hemoglobin conjugate below the molecular weight and degree of polyalkylene oxide substitution parameters set forth above, and preferably contain less than about one weight percent of such species. In addition, the solutions of the present invention are also substantially free of PAO-Hb conjugates having an average degree of substitution of greater than 18. While such heavily conjugated species have not been associated with hemoglobinuria, they are believed to be suboptimal for the purposes of hemoglobin and/or oxygenation of mammalian tissues. Such species can be eliminated from the inventive solutions by controlling the PAO-Hb conjugation reaction and/or separation techniques within the skill of the art.

The polyalkylene oxides include polyethylene glycol (PEG), polypropylene glycol and block copolymers thereof. To be suitable for use in the present invention, the polyalkylene oxides must be soluble in water at room temperature. Therefore, the degree of block copolymerization for the block copolymers should not be so great to render the polymer water insoluble at room temperature. Polyalkylene oxides having molecular weights between about 1,000 and about 80,000 daltons are suitable for use with the present invention. Polyalkylene oxides having molecular weights between about 2,000 and about 50,000 daltons are preferred.

The conjugated hemoglobins can be prepared from hemoglobins from any appropriate mammalian source, human or non-human, depending upon need. At present, the most commercially viable hemoglobins are human and ruminant hemoglobins, particularly bovine hemoglobin. Human hemoglobin can be obtained from whole human blood, either freshly drawn or from the outdated supply of blood banks. Human hemoglobin can also be obtained from placentas or packed erythrocytes obtained from human blood donor centers. The hemoglobin can also be produced by recombinant methods including the establishment of transgenic herds or cells. Such transgenic animals may express wild type human, variant human or mutated human hemoglobin. Solutions of the present invention may also contain mixtures of various conjugated hemoglobins.

Ruminant hemoglobin such as bovine or sheep are also useful. Bovine hemoglobin is obtained, for example, from slaughterhouses or controlled herds. The choice of animal source is not critical, but will instead be made on the basis of commercial demand. The products of the present invention also have veterinary end-uses. Therefore, various animal sources are appropriate for the products and methods of the present invention.

The method by which the hemoglobins have been extracted from erythrocytes is not critical. The extracted hemoglobin preferably has an endotoxin concentration less than about 9.1 EU/mL as measured by gel clot or kinetic turbidometric Limulus Amebocytic Lysate (LAL) assay. The phospholipid level is preferably non-detectable as determined by High Performance Liquid Chromatography (HPLC) lipid assays. Phospholipid levels of up to 0.50 mg/mL, however, are acceptable and can be removed in accordance with the methods described herein.

Preferably, the hemoglobin is separated by the method disclosed in commonly owned U.S. Pat. No. 5,264,555, the disclosure of which is hereby incorporated herein by reference thereto. The hemoglobin has also preferably been purified of endotoxins and phospholipids by the methods disclosed in this patent application.

The conjugate is formed by covalently bonding the hydroxyl terminals of the polyalkylene oxide and the free amino groups of the lysine residues of the hemoglobin. Any art-recognized method for conjugating hydroxyl-terminated polymers with the free amino groups of proteins or polypeptides is suitable for use with the present invention. Typically, the terminal hydroxyl groups are first activated. This refers to the conversion of the hydroxyl group to a functional derivative capable of reacting with the free amino groups.

One example of polyalkylene oxide activation is the cyanuric chloride activation of polyalkylene oxides disclosed in commonly owned U.S. Pat. No. 4,179,337 to Davis. The disclosure of this patent is hereby incorporated herein by reference thereto. Another art-recognized method for activating polyalkylene oxides forms the corresponding succinyl-N-hydroxysuccinimide ester. This well-known procedure is disclosed in Abuchowski et al., *Cancer Biochem. Biophys.*, 7, 175–86 (1984).

In a preferred aspect of the invention, urethane linkages are formed with the protein amino groups and the activated polyalkylene oxides. Preferably, the urethane linkage is formed as described in commonly owned U.S. Pat. No. 5,122,614, the disclosure of which is hereby incorporated by reference. This patent discloses the formation of N-succinimide carbonate derivatives of polyalkylene oxides.

The conjugates of hemoglobin and N-succinimide carbonates of polyalkylene glycols can also be prepared as described in commonly owned U.S. Pat. No. 5,234,903, the disclosures of which is incorporated by reference therein.

Regardless of the conjugation method, the reaction forms a mixture of polyalkylene oxide-conjugated hemoglobins of varying degrees of conjugation. The mixture also includes some residual unconjugated polyalkylene oxides and hemoglobin. This mixture is typically in solution in a reaction buffer containing one or more of phosphate, chloride and bicarbonate anions. The mixture of polyalkylene oxide-conjugated hemoglobin (PAO-Hb) reaction products are preferably fractionated in a buffer solution containing from about 1.0 to about 10.0% PAO-Hb conjugates by weight. Suitable solutions have a pH of from about 8.0 to about 9.0 and preferably from about 8.7 to about 9.0. The buffers also have an osmolality between about 25 and about 110 milliosmoles/kg. Osmolality ranges of between about 33 to about 100 milliosmoles/kg are preferred, while a range of from about 67 to about 100 milliosmoles/kg is especially preferred. The solutions preferably contain one or more buffer salts selected from KCl, NaCl, $K_2HPO_4$, $KH_2PO_4$, $Na_2HPO_4$, $NaH_2PO_4$, $NaHCO_3$, $NABO_4$, $(NH_4)_2CO_3$ and glycine NaOH. Sodium borate buffers are preferred for use in the present invention.

Depending upon the reaction buffer utilized, the solution of conjugated hemoglobins may first have to undergo a buffer exchange. The buffer exchange provides a solution having the required osmolality for fractionation. However, such exchanges are essentially conventional and may be performed by, for example, ultrafiltration. Typically, the polyalkylene oxide-conjugated hemoglobin solution is ultrafiltered across a low molecular weight cut-off (30,000 to 50,000 dalton) membrane.

The fractionation of the polyalkylene oxide-hemoglobin (PAO-Hb) conjugates is preferably carried out by contacting the PAO-Hb conjugates in solution with an anion exchange medium which is capable of selectively binding those conjugates having a molecular weight of less than 85,000 daltons and a degree of substitution of less than five polyalkylene oxide conjugates per hemoglobin molecule. This fractionation is achieved by the fact that the conjugated hemoglobin molecules of various degrees of substitution will have isoelectric points which also vary in a somewhat predictable fashion. For example, the isoelectric point of hemoglobin is determined by the number of available lysine residues available on the surface of the protein. These lysine residues also serve as the point of attachment of polyalkylene oxide conjugates. Therefore, as the degree of substitution of polyalkylene oxide conjugates to hemoglobin increases, the isoionic point decreases, and the ability of the polyalkylene oxide-hemoglobin conjugate to bind to an anion exchange resin weakens.

The use of strongly polar anion exchange resins are especially preferred for the method of the present invention. For this reason, quaternary amine coated anion exchange resins are utilized. The quaternary amine resin may be coated onto either a polymeric or silica matrix; however, polymeric matrices are preferred. A number of tetramethylamine, or quaternary methylamine, anion exchange resins are commercially available, coated onto the support matrices. Included among the commercially available quaternary anion exchange resins suitable for use with the present invention are QA TRISACRYL® and QMA-SPHEROSIL®, quaternary amine resins coated onto a polymer matrix, manufactured by IBF of Garenne, France, for Sepracor of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Millford, Mass. and PEI resins manufactured by J. T. Baker of Phillipsburg, N.J., may also be used.

Conventional liquid chromatography, rather than HPLC is preferably utilized to fractionate the solutions of mixed polyalkylene oxide-hemoglobin conjugates. That is, techniques of HPLC are not critical to the fractionation of mixed solutions of polyalkylene oxide-conjugated hemoglobin. Conventional liquid chromatography is more readily adapted to large-scale commercial production techniques than HPLC. Furthermore, a significant economic advantage is also obtained by a reduction in the cost of equipment, process time and risk of endotoxin contamination.

The chromatography columns should have an axial flow or radial flow design and a diameter between about 1.6 cm and about 1000 cm. The column length should be between about 5 cm and about 1000 cm. Such columns will typically hold between about 1 mL and about 785 L of anion exchange chromatography resins. The chromatography equipment, anion exchange resin, and buffers should be depyrogenated, utilizing standard procedures.

Typically, the anion exchange resin is packed in the column and equilibrated by conventional means. A buffer having the same pH and osmolality as the conjugated hemoglobin solution is used. The conjugated hemoglobin solution is then absorbed onto the column at a rate of about 0.1 to about 0.5 liters a minute. At the completion of the loading, a flow of an elution buffer is applied to the column to elute fractions of polyalkylene oxide-conjugated hemoglobin. The fractions are of essentially uniform molecular weight and degree of substitution.

The elution method is not critical and will depend upon the needs of the end user. A preferred polyalkylene oxide conjugated hemoglobin fraction is collected having a molecular weight greater than about 85,000 daltons and a degree of substitution of five or more polyalkylene oxide conjugates. The fraction can be obtained by a single step elution utilizing an isocratic flow of an elution buffer having a pH and an osmolality within the ranges set forth above. The elution buffer preferably contains one or more salts selected from KCl, NaCl, $K_2HPO_4$, $KH_2PO_4$, $Na_2HPO_4$, $NaH_2PO_4$, $NaHCO_3$, $NaBO_4$ and $(NH_4)_2CO_3$. The preferred fraction is substantially free of lower molecular weight conjugates and hemoglobins with four or fewer polyalkylene oxide conjugates. The lower molecular weight, less conjugated species, as well as any unconjugated hemoglobins can then be backwashed from the column by conventional techniques.

Gradient elution and techniques utilizing multiple isocratic steps of increasing concentration within the osmolality range can also be used. Gradient and multiple isocratic elution steps of increasing concentration will result in the sequential elution of fractions of polyalkylene oxide-hemoglobin conjugates. The degree of polyalkylene oxide-conjugation within each fraction will be substantially uniform. However, the degree of polyalkylene oxide conjugation for each fraction will decrease with elution time. Material captured on the ion exchange resins may also be contacted with various solvents, solutions, detergents and mixtures thereof to effect viral inactivation. For example, chloroform may be used to effect the vital inactivation.

Techniques of flow-through chromatography can also be employed, in which the column is first equilibrated by conventional means with a buffer having the same pH and osmolality as the conjugated hemoglobin solution. The conjugated hemoglobin solution is then loaded onto the column at a rate of about 0.1 to about 0.5 liters a minute. Hemoglobin conjugates having a degree of conjugation associated with hemoglobinuria bind to the column while conjugates that do not cause hemoglobinuria flow through and are immediately collected. The preferred buffer for flow-through chromatography is 20 mM $NaHCO_3$. The preferred chromatography resin is QAE550C®, or Poros HQ, quaternary amine resins coated onto a polymer matrix, manufactured by TosoHaas of Montgomeryville, Pa. or Perseptive Biosystems of Boston, Mass., respectively. The basic elution and flow-through chromatography techniques described herein are essentially conventional and can be applied to the inventive processes with the disclosed buffers and chromatography resins by one of ordinary skill without undue experimentation.

The temperature range for elution is between about 4° C. and about 25° C. Preferably, elution is carried out at a temperature of from about 6° C. to about 150° C. and most preferably at about 8° C. The elution of the polyalkylene oxide-hemoglobin fractions is detected by UV absorbance at 280 nm. Fraction collection may be achieved through simple time elution profiles.

The preferred hemoglobin fractions can then be pooled to provide a solution in the elution buffer of polyalkylene oxide-hemoglobin conjugates. The conjugates have a molecular weight greater than about 85,000 daltons and a degree of substitution which is sufficient to avoid nephrotoxic effects after administration to mammals. In one aspect of the invention, the degree of substitution which avoids nephrotoxic effects is five conjugates or greater. This embodiment is especially useful when PAO strands of relatively low molecular weights, i.e., 2,000–5,000 are used. In another preferred aspect of the invention, the degree of substitution is less than five but nonetheless sufficient to avoid hemoglobinuria-related toxicity. In these aspects of the invention, the conjugates have at least one polyalkylene oxide having a molecular weight which is sufficient to raise the weight of the conjugate to over about 85,000 daltons. As stated above, the hemoglobins useful in the conjugates of the present invention have a molecular weight of about 64,000 daltons. Therefore, at least one PAO strand of molecular weight of at least about 21,000 daltons, whether branched or straight, is conjugated to the hemoglobin to provide the desired conjugate. It will also be understood that the conjugates can include more than one strand, i.e., two or more 20,000 dalton strands to provide the desired weight conjugates. Within this aspect of the invention, PAO-Hb conjugates of the following characteristics are contemplated.

| Hb | PAO MW | STRANDS/Hb | CONJUGATE |
|---|---|---|---|
| 64,000 | 12,000 | 3 | 100,000 |
| 64,000 | 20,000 | 2 | 104,000 |
| 64,000 | 7,500 | 4 | 94,000 |

The foregoing list is not meant to be exclusive and is merely furnished to provide illustrative embodiments. Typically, the pooled fractions have a concentration between about 1.0 and about 10.0 weight percent of the polyalkylene oxide-hemoglobin conjugate, actual amounts will vary, however.

The pooled hemoglobin fractions are preferably included with a physiologically-acceptable carrier such as those well-known to those of ordinary skill in the art. For example, a physiologically-acceptable carrier may have a pH of about 7.8 and include a phosphate/saline buffer system containing NaCl (100 mM), KCl (10 mM), $Na_2HPO_4$ (3 mM) and $NaHCO_3$ (30 mM). If necessary, the pooled fractions may be transferred to a physiologically-acceptable carrier by buffer exchange techniques such as ultrafiltration.

Following the collection of the conjugated hemoglobin fractions, the chromatography column should be washed to remove the materials that have bound to the column. The column can then be re-equilibrated and prepared for another loading of polyalkylene oxide-conjugated hemoglobins to be fractionated.

The present invention also includes the unexpected discovery that when the above-described fractionation methods are carried out, physiologically unacceptable materials can also be simultaneously removed by binding to the anion exchange resins. It has been found, for example, that commonly present by-products which are physiologically unacceptable such as DNA, endotoxins or phospholipids bind to the anion exchange resin. The polyalkylene oxide-conjugated hemoglobins are thus also purified while the conjugates are fractionated. It is preferred, however, that the PAO-Hb conjugates and solutions containing same be rendered substantially free of these impurities before the contacting with the anion exchange resin.

An example of a preferred process is as follows:

About 24 liters of a 5–6 weight percent solution of bovine hemoglobin conjugated with polyethylene glycol (PEG) in 4 mM pH 9.0±0.1 borate buffer is loaded onto a 60 cm long, 25 cm diameter liquid chromatography column. The column is packed with 30 L of quaternary amine anion exchange resin such as DEAE-spherodex (by IBF of Garenne, France) equilibrated with the above buffer. The PEG-hemoglobin solution is loaded at a rate of 0.50 L a minute, and once it is completely absorbed, an isocratic flow of the buffer is started to elute the PEG-hemoglobin from the column. Elution of a PEG-hemoglobin fraction having a degree of conjugation between about 6 and about 11 PEG conjugates per hemoglobin molecule is detected with a UV detector. At this point, collection of the effluent is initiated and continued until the effluent PEG-hemoglobin peak has been reduced to five percent of peak amplitude.

The foregoing procedure produces PEG-hemoglobin fractions that, when pooled, typically have a PEG-hemoglobin concentration within the concentration range of about 1.0 and about 10.0 weight percent, typically about 2.0 weight percent. The pooled fractions typically have an endotoxin level of less than 0.1 EU/mL as measured by gel clot or kinetic turbidometric LAL assay. The phospholipid level is nondetectable as measured by HPLC liquid assay. The pool of fractions can then be stored for extended periods using standard techniques at temperatures of about −20° C. for future use or maintained at temperatures of about 2°–8° C. for immediate use.

It is contemplated that the present method can be applied to fractionate other polymer-hemoglobin conjugates to resolve the polymer conjugate into fractions varying only by the degree of polymer substitution. When buffers of the above-described pH and osmolality are utilized, the method will also purify such other polymer-hemoglobin conjugates of physiologically incompatible materials such as DNA, endotoxins and phospholipids.

This aspect of the present invention provides a versatile process by which polyalkylene oxide-conjugated hemoglobins can be fractionated and at the same time, purified of unwanted materials such as DNA, endotoxins and phospholipids. This permits the isolation of polyalkylene oxide-hemoglobin conjugates which are substantially free of contaminants and substantially avoid causing hemoglobinuria in mammals. Solutions of the conjugates in a pharmaceutically-acceptable carrier are particularly suitable for use as hemoglobin-based cell-free transfusional fluids. Such transfusional fluids are acceptable as alternatives to whole blood or blood fractions for use as oxygen carriers and plasma expanders.

The following non-limiting examples illustrate certain aspects of the invention. These examples are not meant in any way to restrict the effective scope of the invention. All parts and percentages are by weight unless otherwise noted, and all temperatures are in degrees Celsius.

EXAMPLES

Example 1

Preparation of Bovine Hemoglobin-Polyethylene Glycol Conjugate

Frozen bovine hemoglobin (bHb) (12.4%, 25 L) was thawed at 4° C. overnight. The thawed bHb was mixed with 25 l of reaction buffer (0.8 m NaCl and 0.2M $Na_2HPO_4$) to make 50 L of 6.2% bHb solution. The pH was adjusted to 7.8 by adding 1M $KH_2PO_4$ solution while maintaining the temperature at 8° C.±0.2° C. The hemoglobin solution was deoxygenated under nitrogen gas using a gas permeable membrane to achieve a level of 75–80% deoxy-bHb. A 12 molar excess of polyethylene glycol-succinimidyl carbonate (SC-PEG), prepared according to the method of U.S. Pat. No. 5,122,614, was added to the deoxy-bHb solution and the reaction mixture was stirred at 8° C. for 2 hours. When the PEG reaction was completed, 30 mm cysteine was added into the reaction solution and the pH was adjusted to 8.0+0.1 with either 1M $KH_2PO_4$ or NaOH. The reaction solution was then filtered using a 0.22 micron Durapore filter. The reaction solution was then buffer-exchanged to 3.3 mM borate buffer, pH 9.0±0.2 using ultrafiltration equipment (Centrasette 30K).

Example 2

A 30×60 cm column was packed with 30 L DEAE-spherodex (IBF of Garenne, France) in 3.3 mM borate buffer, pH 9.0±0.1. The column was depyrogenated with 0.2 N NaOH and equilibrated with four column volumes (120 L) of depyrogenated 3.3 mM borate buffer, pH 9.0. The capacity of the DEAE-spherodex for PEG-bHb was determined to be 40 mg/ml.

24 L of a 5 weight percent solution of the PEG-bHb of Example 1 was loaded onto the ion exchange column. The balance of the PEG-bHb solution was stored at −20° C. The column was washed with three column volumes (90 L) of 3.3 mm borate buffer, pH 9.0±0.1 to remove unreacted PEG. PEG-bHb was then eluted with 70 L 100 mm borate buffer, pH 9.0.

The eluted PEG-bHb was then buffer exchanged by ultrafiltration into a formulation buffer. The formulation buffer was prepared by dissolving the following salts into 550 L of distilled water:

| | |
|---|---|
| NaCl (100 mm) | 3.2142 kg |
| KCl (10 mm) | 410.08 g |
| Na$_2$HPO$_4$ (3 mm) | 442.31 g |
| NaHCO$_3$ (30 mm) | 1.386 kg |

The pH of the formulation buffer was then adjusted to 7.8±0.1 by adding 1M KH$_2$PO$_4$ (HCl or H$_3$PO$_4$ could also have been used). The buffer exchange was then performed by concentrating the volume of the purified PEG-bHb solution collected from the ion exchange column to approximately 5±0.1 weight percent PEG-bHb using a 50K Centrasette (Filtron) primed with 50 l distilled water and 10 L formulation buffer. Ultrafiltration was continued until 550 l formulation buffer (20 fold) was consumed. The completeness of the dialysis was checked and the resulting solution was then sterile filtered through a Durapore filter (0.22 micron, Millipore) into 300 mL blood bags and stored at −20° C.

The degree of conjugation of the PEG-bHb was determined to be approximately 9 by trinitro-benzenesulfonic acid (TNBS) assay, a well-known technique. The solution was free of phospholipids.

Example 3

A PEG-bHb solution was fractionated according to the procedure of Example 2, except that 67 mM borate buffer was used as the eluting buffer. The average degree of conjugation of the eluted fraction was 11 PEG per hemoglobin molecule, determined by TNBS assay.

Example 4

The PEG-bHb of Example 1 was dialyzed with distilled water to remove excess salt. The dialyzed PEG-bHb was charged on a DEAE-spherodex column, which had been previously equilibrated with 1 mM Na$_2$HPO$_4$ buffer solution, pH 8.03. The column was successively eluted with 2 mM, 5 mM, 10 mM and 50 mM Na$_2$HPO$_4$ buffer solutions, pH 8.03. The collected fractions were concentrated by centrifugation. The fractions were determined to decrease in the degree of conjugation as the concentration of the elution buffer increased.

Example 5

Several PEG-bHb solutions, prepared as described herein were administered to laboratory rats by exchange transfusion (E.T.). In this example, solutions containing varying degrees of PAO-Hb conjugation were transfused to demonstrate the lack of hemoglobinuria in mammals administered the inventive solutions. The test results are depicted in the table below.

TABLE

| SAMPLE | AVG. DEGREE OF CONJUGATION | CONCENTRATION (WT. %) | ET | mg Hb mL Urine |
|---|---|---|---|---|
| 1 | 8.0 | 6.1 | 40 | 0.02 + 0.003 |
| 2 | 8.6 | 4.2 | 60 | 0.04 + 0.004 |
| 3 | 12.0 | 6.2 | 30 | 0.00 |
| 4 | 12.0 | 6.2 | 50 | 0.00 |
| 5 | 12.0 | 6.2 | 70 | 0.00 |

The animals underwent different levels of exchange transfusion in order to achieve similar dosage because the samples were of different concentration. The solutions produced no detectable renal tubular necrosis.

Hemoglobinuria experiments designed to investigate the relationship between hemoglobinuria and renal injury have determined by histopathology that PEG-Hb yielding less than 0.1 mg Hb/mL urine at 50% E.T. causes no detectable renal tubular necrosis after 24 hours, whereas PEG-bHb producing more than 0.1 mg Hb/mL urine results in mild acute tubular necrosis. As can be seen from the table above, those samples depicted above are not associated with renal toxicity or pathological hemoglobinuria.

Example 6

The process of example 1 is repeated except that 12,000 molecular weight PEG was used to conjugate the hemoglobin. Thereafter, the conjugates are placed into an acceptable solution and the PEG-bHb solution is fractionated according to the procedure of Example 2, except that the eluting buffer selected provides conjugates containing an average of about 2 PEG 12,000 strands per hemoglobin molecule as determined by TNBS assay.

Example 7

The process of example 1 is repeated except that 20,000 molecular weight PEG was used to conjugate the hemoglobin. Thereafter, the conjugates are placed into an acceptable solution and the PEG-bHb solution is fractionated according to the procedure of Example 2, except that the eluting buffer selected provides conjugates containing an average of about 2 PEG 20,000 strands per hemoglobin molecule as determined by TNBS assay.

Example 8

Hemoglobin solutions are prepared in the manner described in Example 5 using the products obtained as a result of Examples 6 and 7. In each case, the samples were prepared to contain approximately 6% hemoglobin. The samples are exchange transfused into rats in amounts ranging from about 30 to about 60%. After 24 hours, the amount of hemoglobin excreted in the urine of the rats is found to be below that which is associated with inducing nephrotoxicity.

Numerous variations and combinations of the features set forth above can be utilized without departing from the present invention as set forth in the claims. Such variations are not regarded as a departure from the spirit and scope of the invention. All such modifications are intended to be included within the scope of the following claims.

We claim:

1. A polyalkylene oxide-conjugated hemoglobin-containing solution comprising polyalkylene oxide-conjugated hemoglobin having a molecular weight greater than about 85,000 daltons and a degree of substitution which is less than five polyalkylene oxide conjugates per hemoglobin molecule and sufficient to avoid clinically significant nephrotoxicity in mammals after administration thereof.

2. The solution of claim 1, wherein the concentration of said polyalkylene oxide-conjugated hemoglobin in said solution is from about 1 to about 10 weight percent.

3. The solution of claim 2, wherein said concentration of said polyalkylene oxide-conjugated hemoglobin in said solution is from about 3 to about 7 weight percent.

4. The solution of claim 3, wherein said concentration of said polyalkylene oxide-conjugated hemoglobin in said solution is from about 4 to about 6 weight percent.

5. The solution of claim 1, wherein said polyalkylene oxide-conjugated hemoglobin has a molecular weight between about 90,000 and about 250,000 daltons.

6. The solution of claim 5, wherein said polyalkylene oxide-conjugated hemoglobin has a molecular weight between about 95,000 and about 120,000 daltons.

7. The solution of claim 1, wherein said polyalkylene oxide-conjugated hemoglobin has an average degree of substitution of at least about 1 polyalkylene oxide strand per hemoglobin molecule.

8. The solution of claim 7, wherein said polyalkylene oxide-conjugated hemoglobin has an average degree of substitution of at least about 2 polyalkylene oxide strands per hemoglobin molecule.

9. The solution of claim 8, wherein said polyalkylene oxide-conjugated hemoglobin has an average degree of substitution of at least about 3 polyalkylene oxide strands per hemoglobin molecule.

10. The solution of claim 1, wherein said polyalkylene oxide is selected from the group consisting of polyethylene glycol, polypropylene glycol and block copolymers thereof.

11. The solution of claim 1, wherein said polyalkylene oxide comprises polyethylene glycol.

12. The solution of claim 1, wherein said polyalkylene oxide has a molecular weight between about 1,000 and about 100,000 daltons.

13. The solution of claim 12, wherein said polyalkylene oxide has a molecular weight between about 2,000 and about 50,000 daltons.

14. The solution of claim 13, wherein said polyalkylene oxide has a molecular weight between about 2,000 and about 20,000 daltons.

15. The solution of claim 1, wherein said hemoglobin comprises mammalian hemoglobin.

16. The solution of claim 15, wherein said hemoglobin comprises human hemoglobin.

17. The solution of claim 15, wherein said hemoglobin comprises ruminant hemoglobin.

18. The solution of claim 17, wherein said ruminant hemoglobins comprise bovine hemoglobins.

19. The solution of claim 1, wherein said hemoglobin comprises a hemoglobin produced by recombinant methods.

20. The solution of claim 1, wherein said polyalkylene oxides are conjugated to free amino groups of the lysine residues of said hemoglobin.

21. The solution of claim 19, wherein said polyalkylene oxides are conjugated to said lysine residues of said hemoglobin by means of urethane linkages.

22. A method of simultaneously fractionating and purifying polyalkylene oxide-hemoglobin (PAO-Hb) conjugates, comprising:

(a) contacting PAO-Hb conjugates in solution with an anion exchange medium capable of selectively binding
  (i) PAO-Hb conjugates having a molecular weight of less than about 85,000 daltons and a degree of substitution which is sufficient to cause clinically significant nephrotoxicity in mammals; and
  (ii) physiologically unacceptable materials, so that fractions comprising conjugated hemoglobins having molecular weights greater than about 85,000 daltons and degrees of substitution not associated with clinically significant nephrotoxicity are not bound by said resin; and (b) recovering said fractions comprising conjugated hemoglobin not bound by said resin.

23. The method of claim 22, wherein said anion exchange resin comprises a quaternary amine coated anion exchange resin coated onto a polymeric matrix or a silica matrix.

24. The method of claim 22, wherein said anion exchange medium is selected from the group consisting of quaternary amine coated anion exchange resins and polyethyleneimine coated anion exchange resins.

25. The method of claim 22, wherein said solution containing said PAO-Hb conjugates has a pH of from about 8.0 to about 9.0.

26. The method of claim 25, wherein said solution containing said PAO-Hb conjugates have a pH of from about 8.7 to about 9.0.

27. The method of claim 22, wherein said solution containing said PAO-Hb conjugates has an osmolality of from about 25 to about 110 milliosmoles/kg.

28. The method of claim 27, wherein said solution containing said PAO-Hb conjugates has an osmolality of from about 33 to about 100 milliosmoles/kg.

29. The method of claim 22, wherein said polyalkylene oxide-conjugated hemoglobin is present in said solution in an amount from about 1 to about 10 weight percent.

30. A polyalkylene oxide-conjugated hemoglobin-containing solution comprising polyalkylene oxide-conjugated hemoglobin having less than five polyalkylene oxide conjugates per hemoglobin molecule and a molecular are sufficient to avoid clinically significant nephrotoxicity in mammals after administration thereof.

31. A polyalkylene oxide-conjugated hemoglobin-containing solution comprising polyalkylene oxide-conjugated hemoglobin having a molecular weight and a degree of substitution which are sufficient to substantially avoid hemoglobinuria in excess of 1% of the administered dose of hemoglobin in the urine collected from 0 to 24 hours after administration to a mammal in need thereof.

32. The solution of claim 31, wherein the concentration of said polyalkylene oxide-conjugated hemoglobin in said solution is from about 1 to about 10 weight percent.

33. The solution of claim 32, wherein said concentration of said polyalkylene oxide-conjugated hemoglobin in said solution is from about 3 to about 7 weight percent.

34. The solution of claim 33, wherein said concentration of said polyalkylene oxide-conjugated hemoglobin in said solution is from about 4 to about 6 weight percent.

35. The solution of claim 32, wherein said polyalkylene oxide-conjugated hemoglobin has a molecular weight between about 90,000 and about 250,000 daltons.

36. The solution of claim 35, wherein said polyalkylene oxide-conjugated hemoglobin has a molecular weight between about 95,000 and about 120,000 daltons.

37. The solution of claim 31, wherein said polyalkylene oxide-conjugated hemoglobin has an average degree of substitution of at least about 1 polyalkylene oxide strand per hemoglobin molecule.

38. The solution of claim 37, wherein said polyalkylene oxide-conjugated hemoglobin has an average degree of substitution of at least about 2 polyalkylene oxide strands per hemoglobin molecule.

39. The solution of claim 38, wherein said polyalkylene oxide-conjugated hemoglobin has an average degree of substitution of at least about 3 polyalkylene oxide strands per hemoglobin molecule.

40. The solution of claim 31, wherein said polyalkylene oxide is selected from the group consisting of polyethylene glycol, polypropylene glycol and block copolymers thereof.

41. The solution of claim 31, wherein said polyalkylene oxide comprises polyethylene glycol.

42. The solution of claim 31, wherein said polyalkylene oxide has a molecular weight between about 1,000 and about 100,000 daltons.

43. The solution of claim 42, wherein said polyalkylene oxide has a molecular weight between about 2,000 and about 50,000 daltons.

44. The solution of claim 43, wherein said polyalkylene oxide has a molecular weight between about 2,000 and about 20,000 daltons.

45. The solution of claim 31, wherein said hemoglobin comprises mammalian hemoglobin.

46. The solution of claim 45, wherein said hemoglobin comprises human hemoglobin.

47. The solution of claim 45, wherein said hemoglobin comprises ruminant hemoglobin.

48. The solution of claim 47, wherein said ruminant hemoglobin comprises bovine hemoglobins.

49. The solution of claim 31, wherein said hemoglobin comprises a hemoglobin produced by recombinant methods.

50. The solution of claim 31, wherein said polyalkylene oxides are conjugated to free amino groups of the lysine residues of said hemoglobin.

51. The solution of claim 50, wherein said polyalkylene oxides are conjugated to said lysine residues of said hemoglobin by means of urethane linkages.

* * * * *

UNITED STATES PATENT AND TRADEMARK OFFICE
CERTIFICATE OF CORRECTION

PATENT NO. : 5,650,388
DATED : July 22, 1997
INVENTOR(S) : SHORR, Robert G.L. et al.

It is certified that error appears in the above-identified patent and that said Letters Patent is hereby corrected as shown below:

Column 7, line 49: "chromatographyresins" should read —chromatography resins—.

Column 9, line 51: after "containing" insert —the—.

Claim 30, at line 4: after "molecular" insert —weight and a degree of substitution which—.

Signed and Sealed this

Sixth Day of January, 1998

*Attest:*

BRUCE LEHMAN

*Attesting Officer*  Commissioner of Patents and Trademarks